United States Patent [19]
Hayashi

[11] Patent Number: 6,006,583
[45] Date of Patent: Dec. 28, 1999

[54] ODOR CONCENTRATION MEASURING DEVICE

[75] Inventor: Yoshikazu Hayashi, Inuyama, Japan

[73] Assignee: Kikusui Chemical Industries Co., Ltd., Nagoya, Japan

[21] Appl. No.: 09/129,374

[22] Filed: Aug. 5, 1998

[30] Foreign Application Priority Data

Aug. 8, 1997 [JP] Japan .................................. 9-215159

[51] Int. Cl.⁶ ....................................................... G01N 7/00
[52] U.S. Cl. ........................................... 73/23.34; 600/303
[58] Field of Search ............................ 73/23.34; 600/303

[56] References Cited

U.S. PATENT DOCUMENTS

| | | | |
|---|---|---|---|
| 3,885,550 | 5/1975 | MacLeod | 600/303 |
| 4,265,248 | 5/1981 | MacLeod | 600/303 |
| 4,884,435 | 12/1989 | Ehara | 73/23.34 |
| 5,767,385 | 6/1998 | Bundy et al. | 73/23.34 |

*Primary Examiner*—Hezron Williams
*Assistant Examiner*—Jay L. Politzer
*Attorney, Agent, or Firm*—Davis and Bujold

[57] ABSTRACT

There is disclosed an odor concentration measuring device which can objectively and easily measure an odor concentration. The odor concentration measuring device 1 is provided with an injector having a cylinder 3 and a piston 5, and an odor sensor 11 is fixed to an inner wall 3a of the cylinder 3. The odor sensor 11 measures the odor of air inside the cylinder 3, and outputs a voltage V in accordance with the odor intensity. A control box 7 provided on the outer periphery of the cylinder 3 is provided with an electronic control circuit, which allows a blue LED 9b to light instead of a red LED 9r when the voltage V reaches a value corresponding to the odor intensity which cannot be perceived by people. By reciprocating the piston 5, the sample air is diluted. The odor concentration can be measured by the dilution magnification at which the lighting state of the LED 9r or 9b is changed. Since the odor concentration is measured by the dilution magnification, measurement results which satisfactorily correspond to human olfaction can be obtained.

17 Claims, 4 Drawing Sheets

ODOR CONCENTRATION MEASURING DEVICE

BACKGROUND OF THE INVENTION (i) Field of the Invention

The present invention relates to an odor concentration measuring device for measuring the odor concentration of a sample gas.

(ii) Description of the Related Art

Recently, problems of malodor pollution together with noise pollution and environmental pollution have been raised. As a conventional method of measuring the odor intensity, an injector method has been heretofore used as described later. For example, the injector method specified by ASTM (American Society for Testing and Materials) and its modification adapted for use in Japan.

In the injector method, the first predetermined amount Vs, e.g., 2 ml of sample air is taken into an injector cylinder. Subsequently, odorless air is taken into the cylinder to obtain the second predetermined amount, e.g., 100 ml of the volume in the cylinder. The sample air is then diluted at the dilution magnification of 100/Vs which is determined by the predetermined amounts. After the cylinder is left to stand for 15 seconds or longer to diffuse the sample air, observers smell odor while pushing the air out of the cylinder. After the volume inside the cylinder reaches Vs, the odorless air is again taken into the cylinder to repeat the aforementioned operation. The maximum dilution magnification at which the observers can perceive the odor by repeating the operation is measured, and used as the index of odor concentration.

Additionally, in the injector method, the sample air may be taken only once for one measurement. Therefore, the odor of a smaller amount of sample air can be measured at various dilution magnifications as compared with a three-point comparison odor bag method in which an odor bag filled with sample air of each dilution magnification is used.

Moreover, various methods are studied separate from the injector method. For example, an odor sensor is constituted of a semiconductor gas sensor or a quartz oscillator to which an artificial lipid bilayer is attached, and disposed in sample air, so that the odor intensity of the sample air is detected with an output from the odor sensor.

In the injector method, however, there are personal differences among the observers. Therefore, the odor concentration needs to be obtained by totally judging measurement results of the maximum dilution magnification by many observers. Furthermore, observers' hands, clothes and the like need to be clean and odorless. The observers have to avoid having food with long-lasting odor in their mouths. They also have to avoid smoking, chewing gum or tobacco or eating immediately, e.g., within 30 minutes before the measurement. Furthermore, observers who have a cold or are in physical conditions adversely affecting their olfaction need to be excluded. Measurement has to be performed only by the observers who are in good physical conditions.

As aforementioned, the injector method requires a large number of observers and careful preparations. Moreover, even when the odor concentration is measured through such a laborious operation, there is a possibility that differences in olfaction with people are reflected. It cannot be said that the measurement results are sufficiently objective.

Furthermore, in the method using the odor sensor, a correlation between the sensor output and the human olfaction has not been found yet. Therefore, the results of the odor concentration measurement by the odor sensor are used only for reference. In order to grasp the realities of the odor pollution and the like, measurements have to be finally performed in the injector method or the three-point comparison odor bag method.

SUMMARY OF THE INVENTION

Wherefore, an object of the invention is to provide an odor concentration measuring device which can objectively and easily measure an odor concentration.

To attain this and other objects, the present invention provides an odor concentration measuring device which has an injector provided with a cylinder at least partially opened to the outside and a piston engaged with the cylinder. It can be detected that a volume inside the cylinder reaches at least two different reference values. The odor concentration measuring device is also provided with an odor measuring unit for measuring the odor inside the cylinder and an output unit for outputting measurement results of the odor measuring unit.

In the invention, the volume inside the cylinder is changed by sliding the piston of the injector. It can be detected that the volume reaches two reference values. The smaller one of the two reference values is hereinafter referred to as Vs while the larger one is referred to as Vl. After sample air is taken into the cylinder until the volume inside the cylinder reaches Vs, odorless air is taken into the cylinder to obtain the volume Vl. Then, the sample air can be diluted Vl/Vs times. The odor measuring unit measures the odor inside the cylinder, and the output unit outputs the measurement results. By observing the outputted measurement results while repeating the dilution, and by measuring the dilution magnification at which the measurement result corresponds to the odor which can be perceived by people, the odor concentration can be measured in the same manner as in the injector method. Moreover, the measurement of the dilution magnification does not need to depend on human senses. Therefore, observers do not need to be prepared, and the odor concentration can be objectively measured.

According to the invention, the odor concentration can be objectively and easily measured. Furthermore, in the invention, instead of converting the output of the odor measuring unit to the odor concentration as it is, the dilution magnification at which the output corresponds to the odor which can be perceived by people is measured. Therefore, the odor concentration measured according to the invention satisfactorily corresponds to the human olfaction. Even if a relatively inexpensive sensor is used as the odor measuring unit, a sufficient measurement precision can be obtained. Moreover, the odor measuring unit and the output unit of the invention can be constituted of small-sized elements. In this case, the odor concentration measuring device can be easily carried, and the field investigation of various odor concentrations is effectively facilitated.

In the invention, the output unit determines whether or not the measured value of the odor measuring unit exceeds the predetermined value, and emits an output in accordance with a determination result.

In the injector method, as aforementioned, the dilution magnification or odor concentration is measured dependent on whether or not the observers can perceive the odor of the diluted sample air. When the value corresponding to the odor which can be perceived by people is set as the predetermined value, the output of the output means can indicate whether or not the observer can perceive the odor of the diluted sample air. The odor concentration can be measured based on the output of the output unit in the same manner as the conventional injector method. Therefore, the invention has an advantage that the odor concentration can be easily and accurately measured.

In the invention, the odor measuring unit and the output unit are detachably attached to the injector.

In the injector method, there is a possibility that odor substances are adsorbed by sliding surfaces on the inside of the cylinder and the outside of the piston. It is, therefore, pointed out that in a case where the odor concentration needs to be measured with a remarkable high precision, the injector needs to be disposable. In the invention, since the odor measuring unit and the output unit are detachably attached to the injector, the odor measuring unit and the output unit can be detached from the injector, so that only the injector can be replaced with a new one. Even if the injector is disposable, the expensive odor measuring unit and the output unit can be reused. Therefore, the invention further has an advantage that even in the case where the odor concentration is measured with a remarkable high precision, the measurement cost can be effectively reduced.

In the invention, the odor concentration measuring device is provided with a stop unit for stopping the piston from sliding when the piston is slid until the volume in the cylinder reaches at least one of the reference values.

In the injector method, as aforementioned, by changing the volume in the cylinder between the two reference values, the sample air needs to be repeatedly diluted. On the other hand, the stop unit of the invention stops the piston from sliding when the volume in the cylinder reaches at least one of the reference values. Therefore, the operation of the piston for repeating the dilution is further facilitated. The invention has an advantage that the odor concentration can be easily measured.

In the invention, the odor concentration measuring device further has a filter disposed in the opening in the cylinder for purifying the air flowing into the cylinder via the opening to obtain odorless air.

In the injector method, as aforementioned, the sample air needs to be diluted by supplying odorless air into the cylinder. The diluting operation has to be performed in the atmosphere of odorless air. On the other hand, in the invention, the opening of the cylinder is provided with a filter for purifying and making odorless the air which flows into the cylinder via the opening. Therefore, even if the air in the atmosphere has a slight odor, the air is purified to become odorless when flowing into the cylinder via the filter. Therefore, the diluting operation does not need to be performed in the atmosphere of odorless air. The invention has an advantage that the odor concentration can be measured easily and accurately.

DETAILED DESCRIPTION OF THE PREFERRED EMBODIMENTS

Figure 1:
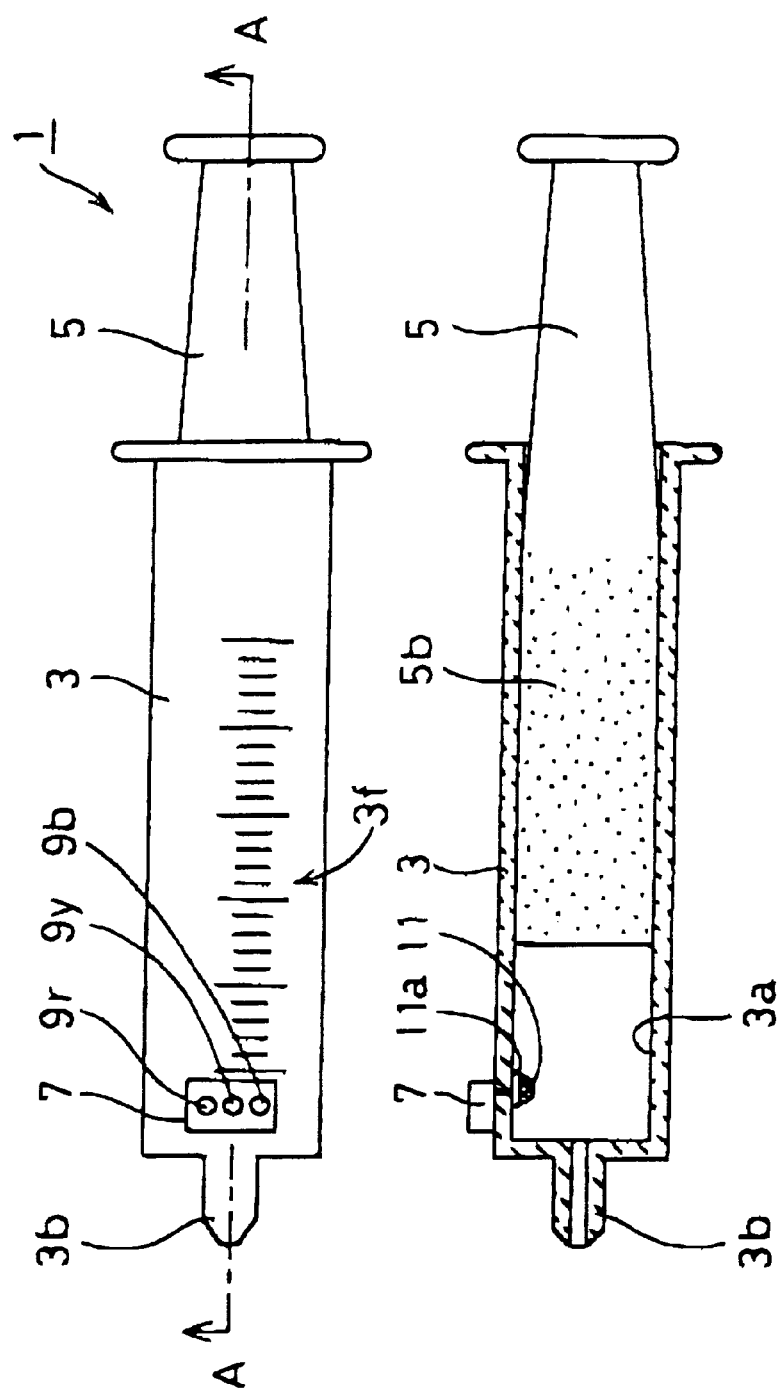
FIG. 1A is a plan view showing an odor concentration measuring device embodying the invention.
FIG. 1B is a sectional view of a cylinder taken along line A—A in FIG. 1A.

An embodiment of the invention will be described with reference to the accompanying drawings As shown in FIGS. 1A and 1B, the odor concentration measuring device 1 is provided with an injector having a glass cylinder 3 and a piston 5. On an outer periphery of the piston 5 hermetically engaged in the cylinder 3, a sliding surface with an inner wall 3a of the cylinder 3 is formed of a ground glass 5b. Additionally, a tip end of the cylinder 3 opposite to the piston 5 is protruded and provided with an opening 3b, and graduations 3f are formed on an outer periphery of the cylinder 3. When the piston 5 is pulled, the atmospheric air is drawn into the cylinder 3 via the opening 3b. When the piston 5 is pushed, the air in the cylinder 3 is discharged via the opening 3b. By reading the graduation 3f with which the tip end of the piston 5 is aligned, the volume inside the cylinder 3 can be detected, On the outer periphery of the cylinder 3, a rectangular parallelepiped control box 7 is fixed in the vicinity of the tip end of the cylinder 3. Each longitudinal side of the control box 7 is substantially the same in magnitude as the radius of the cylinder 3. Red, yellow and blue LEDs 9r, 9y and 9b are disposed on the surface of the control box 7, respectively. A hemispherical odor sensor 11 is fixed via a base 11a onto the inner wall 3a of the cylinder 3 adjacent to the control box 7. The odor sensor 11 is constituted of a semiconductor gas sensor or a quartz oscillator to which an artificial lipid bilayer is attached. By measuring the odor of the air inside the cylinder 3, the odor sensor 11 outputs a voltage V in accordance with the intensity of the odor.

Figure 2:
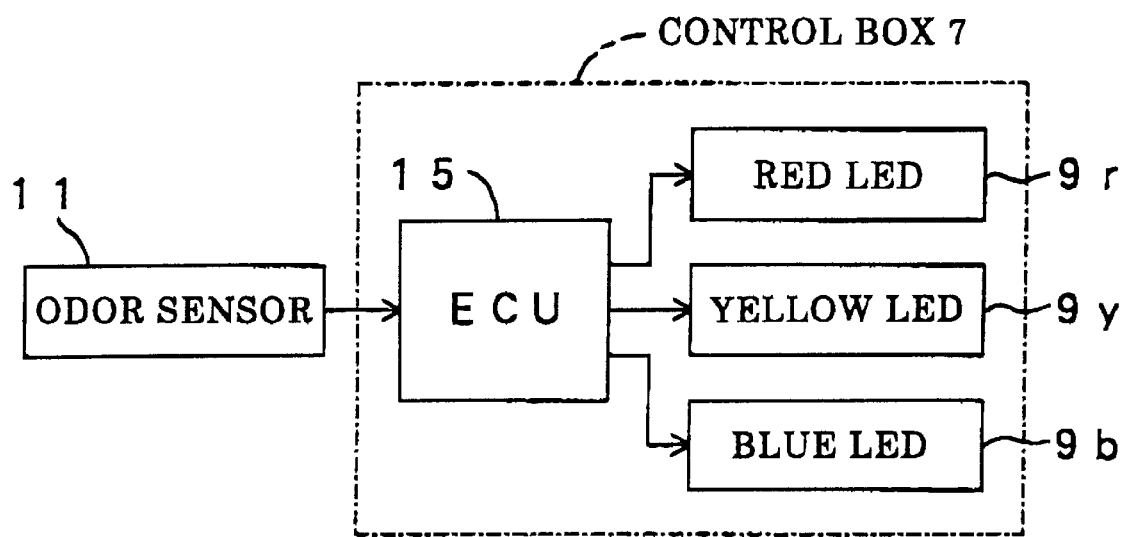
FIG. 2 is a block diagram showing a structure of a control box for controlling the odor concentration measuring device.

The constitution of the control box 7 will be described with reference to FIG. 2. The control box 7 is provided with an electronic control circuit (ECU) 15 which is constituted of a known microcomputer provided with CPU, ROM, RAM and the like. The output voltage V of the odor sensor 11 is transmitted to the electronic control circuit 15. The electronic control circuit 15 executes an odor concentration measuring process as described later based on the output voltage V of the odor sensor 11, and controls the lighting of LEDs 9r, 9y and 9b.

Figure 3:
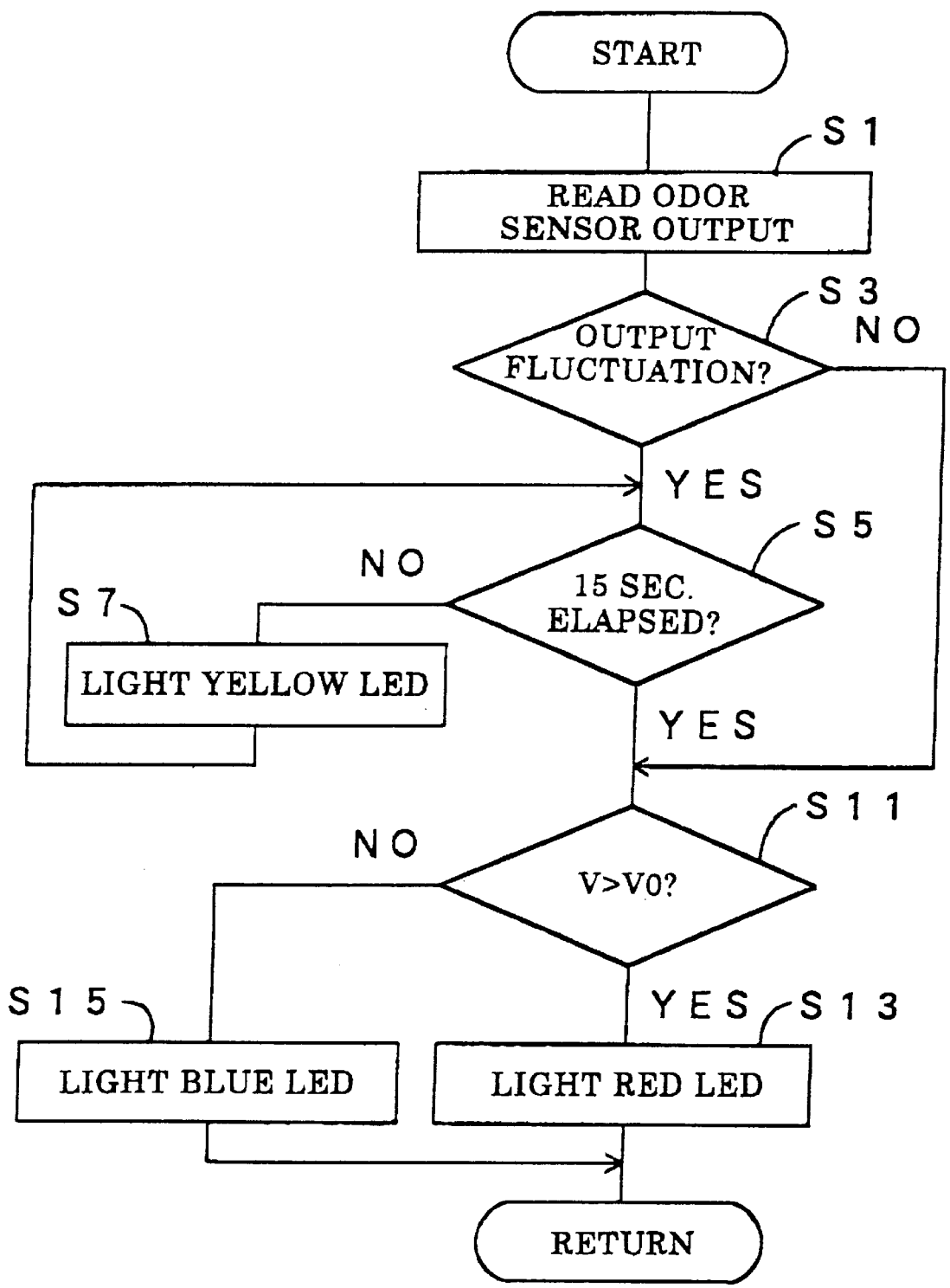
FIG. 3 is a flowchart showing an odor concentration measuring process executed in the device.

FIG. 3 is a flowchart showing the odor concentration measuring process. The electronic control circuit 15 repeatedly executes the process every predetermined cycle, e.g., every 20 milliseconds. As shown in FIG. 3, after starting the process, the electronic control circuit 15 first reads the output voltage V of the odor sensor 11 at step S1. Subsequently, it is judged at step S3 whether or not there is a fluctuation in the output voltage V. If it is determined that the fluctuation occurs (S3:YES), it is determined at step S5 whether or not 15 seconds have elapsed after the output fluctuation. If 15 seconds have not elapsed (S5:NO), the yellow LED 9y is allowed to emit light at step S7, and the process returns to step 5. After it is judged that 15 seconds have elapsed (S5:YES), the process shifts to step S11. Moreover, if it is determined that there is no fluctuation in output at step S3 (S3:NO), the process shifts directly to step S11.

Here, in a case where the sample air whose odor concentration is to be measured or the odorless air for diluting the sample air is drawn into the cylinder 3, the output voltage V of the odor sensor 11 fluctuates. In this case, in order to measure the intensity of odor in the cylinder 3, the cylinder 3 needs to be left to stand for the predetermined time, e.g., 15 second to diffuse the odor uniformly. In the steps S3 to S7, in the case where there is a fluctuation in the output voltage V (S3:YES), the process is on standby for 15 seconds while the yellow LED 9y is lit (S5, S7). Moreover, in the case where there is no output fluctuation (S3:NO), neither sample air nor odorless air is drawn in. In this case, since uniform diffusion does not need to be performed, the process shifts directly to the step S11 and subsequent steps.

It is determined at step S11 whether or not the output voltage V exceeds a predetermined voltage V0. In a case of V>V0 (S11:YES), after the red LED 9r is lit at step S13, the process once ends. In a case where the output voltage V is equal to or less than the predetermined voltage V0 (S11:NO), after the blue LED 9b is lit at step S15, the process once ends. Additionally, when the LED 9y, 9r or 9b is lit at the step S7, S13 or S15, the other LEDs are turned off.

The predetermined voltage V0 corresponds to the intensity of odor which can be perceived by people. Therefore, the odor concentration of the sample air can be measured in the odor concentration measuring device 1 as follows:

First, vaseline or the like is removed from the cylinder 3 and the piston 5 with odorless cleanser and neutral detergent. The cylinder 3 and the piston 5 are dried separately in an odorless room. Subsequently, the sample air sampled in a separate sampling injector (not shown) is moved to the cylinder 3 by a predetermined amount Vs, e.g., 2 ml while confirming the amount with the graduations 3f. In this case, the opening of the sampling injector and the opening 3b of the cylinder 3 may be interconnected by using a transfer syringe specified by ASTM or by using a silicone rubber tube or the like. In order to avoid the mixture of atmospheric air, the sample air is preferably moved by pushing a sampling injector piston without pulling the piston 5 of the injector for the order concentration measuring device 1.

Subsequently, the odor concentration measuring device 1 is disposed in the atmosphere of odorless air, and the odorless air is drawn into by pulling the piston 5. For example, when the volume inside the cylinder 3 is 100 ml, the sample air is diluted at the dilution magnification of 100/Vs. As aforementioned, the yellow LED 9y is lit for 15 seconds after the dilution (S7), but after 15 seconds elapse and the sample air is diffused uniformly, the red LED 9r or the blue LED 9b is lit in accordance with the intensity of the sample-air odor (S13, S15). When the red LED 9r is lit (S13), the odor which can be perceived by people remains in the diluted sample air (V>V0). Therefore, by pushing the piston 5 to set the volume in the cylinder 3 to Vs, the aforementioned diluting operation is repeated. While the diluting operation is repeated, the blue LED 9b is lit (S15). In this case, the odor which can be perceived by people does not remain in the sample air in the cylinder 3 (VS≦V0). The dilution magnification at this time is set as the maximum dilution magnification determined in the injector method, and used as the index of the sample-air odor concentration.

As aforementioned, in the odor concentration measuring device 1, by comparing the output voltage V of the odor sensor 11 with the predetermined voltage V0, the odor concentration can be measured in the same manner as in the injector method. Moreover, the measurement of the dilution magnification does not need to depend on human senses. Therefore, the preparation of observers is unnecessary, and the odor concentration can be objectively measured. The odor concentration can be measured objectively, precisely and easily. Additionally, in the odor concentration measuring device 1, instead of converting the output of the odor sensor 11 to the odor concentration as it is, the dilution magnification at which the output of the odor sensor 11 corresponds to the odor which can be perceived by people is measured. Therefore, the odor concentration measured by the odor concentration measuring device 1 satisfactorily corresponds to the human olfaction. Even if a relatively inexpensive sensor is used as the odor sensor 11, a sufficient measurement precision can be obtained.

Furthermore, the odor sensor 11 and the control box 7 are constituted of small-sized elements, and sufficiently smaller than the cylinder 3. Therefore, the odor concentration measuring device 1 can be easily carried, and the field investigation of various odor concentrations can be easily performed. Moreover, in the odor concentration measuring device 1, the output unit or LED 9r or 9b neither lights nor outputs the measurement result of the odor measuring unit or odor sensor 11 until the sample air in the cylinder 3 is diffused uniformly. Therefore, the odor concentration is prevented from being measured based on the output voltage V of the odor sensor 11 before the uniform diffusion is completed. The odor concentration can be measured precisely.

Figure 4A:
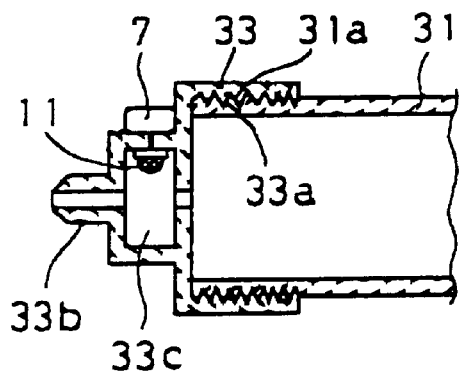
FIGS. 4A to 4D are sectional views showing modifications of the odor concentration measuring device of the invention.

The odor sensor 11 and the control box 7 may be detachably attached to the injector. In a modification shown in FIG. 4A, a cylindrical portion 31 and a tip end 33 which constitute the cylinder 3 are engaged with each other via thread portions 31a and 33a. Moreover, the odor sensor 11 is disposed inside a space 33c formed in a proximal end of an opening 33b, and the control box 7 is fixed on the outer periphery of the space 33c. In the modification, the odor sensor 11 and the control box 7 are detachably attached to the cylindrical portion 31 and the piston 5. The constitution results in the following effect:

Specifically, there is a possibility in the injector method that odor substances are adsorbed by the ground glass 5b of the piston 5 shown in FIG. 1. It is, therefore, pointed out that in a case where the odor concentration needs to be measured with a remarkable high precision, the injector needs to be disposable. In the modification of FIG. 4A, however, by detaching the odor sensor 11 and the control box 7, only the injector including the cylindrical portion 31 and the piston 5 can be replaced with a new one. In this case, even if the injector is disposable, the expensive odor sensor 11 and the control box 7 including the LEDs 9r, 9y and 9b can be reused Therefore, even when the odor concentration is measured with a remarkably high precision, the measurement cost can be effectively reduced.

Figure 4B:
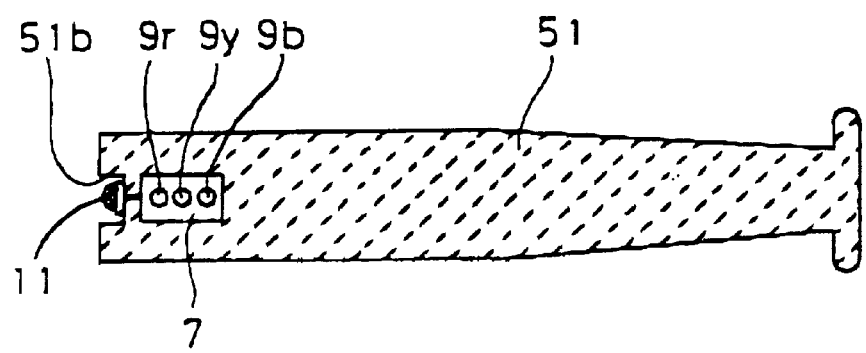

In a modification shown in FIG. 4B, a piston 51 has a recess 51b in its tip end, so that the odor sensor 11 is fixed in the recess 51b. In this case, the change of the volume inside the cylinder 3 caused by the provision of the odor sensor 11 can be minimized. Therefore, when a injector in the marketing is modified as shown in FIG. 4B to form the odor concentration measuring device of the invention, the reliability of the graduations 3f is further enhanced. Furthermore, in this case, the control box 7 is preferably embedded in the piston 51 as shown in FIG. 4B.

Figure 4C:
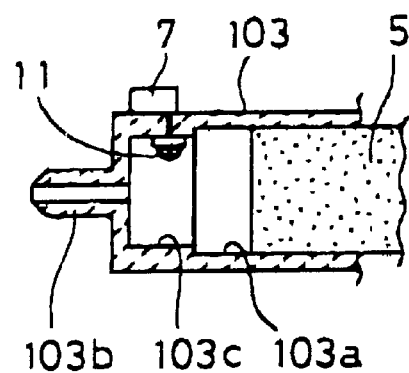

In a modification shown in FIG. 4C, a cylinder 103 has a step portion 103c protruded inwardly from an inner wall 103a in the vicinity of the tip end of the cylinder 103. In this case, when the piston 5 is pushed, the tip end of the piston 5 is engaged with the step portion 103c, and the piston 5 does not slide afterwards. By setting the volume in such a manner that the volume inside the cylinder 103 reaches Vs when the piston 5 is engaged with the step portion 103c, the diluting operation is facilitated as follows. Specifically, when the sample air is discharged via the opening 103b, the volume Vs is obtained simply by continuing to push the piston 5 until the piston 5 is stopped by the step portion 103c. The odor concentration can be measured more easily.

The odor concentration measuring device may be constituted in such a manner that the piston 5 is stopped from sliding when the piston 5 is pulled until the volume inside the cylinder 103 reaches 100 ml. Even in the constitution, the odor concentration can be easily measured in the same manner. Furthermore, if the step portion 103c is provided in the constitution, the odor concentration can be measured more easily. In order to stop the piston 5, the odor sensor 11 or the base 11a may be engaged with the piston 5. In this case, the constitution can be simplified to effectively reduce the manufacture cost.

Figure 4D:
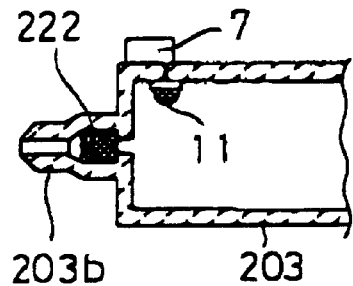

In a modification shown in FIG. 4D, an opening 203b of a cylinder 203 is provided with a filter 222 for purifying air which flows into the cylinder 203 via the opening 203b. The filter 222 has a known constitution in which active carbon is used. The air passed through the filter 222 becomes a standard odorless air. In the constitution, even if atmospheric air has a slight odor, the air can be purified and made odorless by passing the air into the cylinder 203 through the filter 222. Therefore, the diluting operation does not need to be performed in the atmosphere of odorless air. In this case, the odor concentration can be measured easily and precisely. Especially, the field investigation of the odor concentration is remarkably facilitated.

Moreover, by embedding a magnetic body in the piston 5 and disposing Hall element in a predetermined position of the cylinder 3, the frequency with which the piston 5 slides can be counted based on an output of Hall element. In this case, the frequency with which the dilution is performed does not need to be memorized. Therefore, the odor concentration can be measured more easily.

Furthermore, in the embodiment, the LEDs 9r and 9b are used as the output units, but a loudspeaker may be used for generating a voice in accordance with the output voltage V. Alternatively, the output voltage V may be displayed in a numerical value as it is. Specifically, when the diluting operation is continued, the output voltage V converges to a certain predetermined value. Therefore, the predetermined voltage V0 is set based on the converged value, and the odor concentration is measured from the dilution magnification at a time when the output voltage V lowers below the predetermined voltage V0. In this case, even if the output characteristics of the odor sensor 11 vary with an elapse of time, the odor concentration can be measured precisely by setting the predetermined voltage V0 again.

Moreover, when the predetermined voltage V0 is set slightly higher than the aforementioned value, the following operation method is possible. Specifically, in a case where a slight odor remains in the sample air even when the blue LED 9b is lit, the measurement after the blue LED 9b is lit is performed by human senses in a conventional manner. This method is also effective in a case of the measurement of the odor concentration which cannot but depend on human senses. Furthermore, the graduations 3f are provided on the cylinder 3 in the embodiment, but the graduations 3f can be omitted if it can be detected that the volume in the cylinder 3 reaches at least two different reference values, e.g., Vs and 100 ml in the embodiment.

The present invention is not limited to the embodiment described above, and can be variously modified within the scope of the invention as defined by the appended claims.

What is claimed is:

1. An odor concentration measuring device comprising:
   an injector provided with a cylinder having an opening at least partially opened to the outside and a piston being slidably engaged within the cylinder, the injector being able to detect when a volume inside said cylinder reaches at least first and second referenced values;
   an electro-mechanical odor measuring apparatus being affixed to said injector for measuring an odor inside said cylinder; and
   an output means for outputting measurement results of the odor measuring apparatus.

2. The odor concentration measuring device according to claim 1 wherein said output means determines whether or not a measured value of said odor measuring means exceeds a predetermined value, and emits an output in accordance with the determination.

3. The odor concentration measuring device according to claim 1 wherein said odor measuring apparatus and said output means are detachably affixed to said injector.

4. The odor concentration measuring device according to claim 1 wherein the odor concentration measuring device further comprises stop means for stopping said piston from sliding when said volume inside said cylinder reaches at least one of said first and second reference values.

5. The odor concentration measuring device according to claim 1 which further comprises a filter disposed in said opening of said cylinder for purifying and creating odorless air which flows into said cylinder via the opening.

6. The odor concentration measuring device according to claim 1, wherein said electro-mechanical odor measuring apparatus comprises one of a semi-conductor gas sensor and a quartz oscillator which has an artificial lipid bi-layer attached thereto.

7. The odor concentration measuring device according to claim 6, wherein said odor measuring apparatus detects at least first and second voltage values in accordance with an intensity of an odor contained within the cylinder.

8. The odor concentration measuring device according to claim 7, wherein said odor measuring apparatus further comprises an electronic control circuit for determining whether a fluctuation between the first and second voltage values exists, and for supplying a first sensory output to indicate to a user that the fluctuation is occurring.

9. The electronic control circuit according to claim 8, wherein, when said circuit determines that no fluctuation exists between said first and second values, said circuit supplies a final sensory output to the user.

10. The electronic control circuit according to claim 8, wherein said first sensory output is one of a visible and auditory signal and said second sensory output is one of a different visible and auditory signal.

11. An odor concentration measuring device comprising:
    a receptacle having a piston being slidably disposed therein, the receptacle further having an opening through which said piston induces one of an inward and an outward fluid flow of fluid located with said receptacle;
    a detector for detecting a first odorous fluid volume induced to flow into said receptacle by said piston and a second diluting fluid volume induced to flow into said receptacle by said piston;
    an electro-mechanical odor measuring apparatus for measuring a ratio of a dilution magnification based on said first volume and second fluid volume and obtaining an odor concentration value of the fluid being located inside said receptacle; and output means for indicating the odor concentration value of the odor measuring apparatus.

12. The odor concentration measuring device according to claim 11, wherein said electro-mechanical odor measuring apparatus comprises one of a semi-conductor gas sensor and a quartz oscillator which has an artificial lipid bi-layer attached thereto.

13. The odor concentration measuring device according to claim 12, wherein said odor measuring apparatus detects at least a first voltage value and a second voltage value in accordance with the odor concentration located inside the receptacle.

14. The odor concentration measuring device according to claim 13, wherein said odor measuring apparatus further comprises an electronic control circuit for determining whether a fluctuation exists between the first voltage value and the second voltage value, and for supplying a first sensory output to indicate to a user that the fluctuation is occurring.

15. The electronic control circuit according to claim 14, wherein, when said circuit determines that no fluctuation exists between said first value and second value, said circuit supplies a final sensory output to the user.

16. The electronic control circuit according to claim 15, wherein said first sensory output is one of a visible and auditory signal and said second sensory output is one of a different visible and auditory signal.

17. A method of measuring an odor concentration in a sample of air utilizing an odor concentration device, the method comprising the steps of:

a) affixing an electro-mechanical odor measuring device, for outputting a value indicative of an odor concentration, to an injector having a piston and a cylinder defining a predetermined volume;

b) collecting a first volume of odorous air within said cylinder;

c) diluting the first volume of odorous air by introducing a second volume of odorless air into said cylinder via said piston;

d) obtaining a measurement value indicative of the odor concentration measured by the electro-mechanical odor measuring device of the combined first and second volumes of odorous air;

e) removing the second volume of odorous air from said cylinder via said piston and thereby leaving the first volume of odorous air within the cylinder;

f) repeating the above step c through step e until a measurement value is lower than a predetermined value; and g) measuring a ratio of a dilution magnification based on said first volume and said second volume and a number of times the diluting step and the obtaining a value indicative of odor intensity step occurred.

* * * * *